United States Patent [19]

Price

[11] Patent Number: 5,253,643
[45] Date of Patent: Oct. 19, 1993

[54] ORAL AIRWAY FOR DEMOUNTABLY ATTACHING AN ENDOTRACHEAL TUBE

[75] Inventor: Evelyn C. Price, San Antonio, Tex.

[73] Assignees: Evelyn C. Price, Betsy J. Nielson, & Robert E. Gohlke, a partnership, San Antonio, Tex.; Betsy J. Nielson

[21] Appl. No.: 820,305

[22] Filed: Jan. 13, 1992

[51] Int. Cl.⁵ .............................. A61M 25/02
[52] U.S. Cl. .................. 128/207.14; 128/200.24; 128/DIG. 26; 604/174
[58] Field of Search ............ 128/207.14, 207.17, 128/200.26, 911, 912, DIG. 26, 200.24; 604/174, 178

[56] References Cited

U.S. PATENT DOCUMENTS

| | | | |
|---|---|---|---|
| 2,127,215 | 8/1938 | Gwathmey | 128/207.14 |
| 2,908,269 | 10/1959 | Cheng | 128/207.14 X |
| 3,542,321 | 11/1970 | Kahabka | 128/DIG. 26 X |
| 3,774,616 | 11/1973 | White | 128/DIG. 26 X |
| 4,054,135 | 10/1977 | Berman | 128/207.14 X |
| 4,270,529 | 6/1981 | Muto | 128/200.26 |
| 4,338,930 | 7/1982 | Williams | 128/200.26 |
| 4,351,331 | 9/1982 | Gereg | 128/207.17 |
| 5,069,206 | 12/1991 | Crosbie | 128/207.17 |

FOREIGN PATENT DOCUMENTS

| | | | |
|---|---|---|---|
| 2371934 | 7/1978 | France | 128/207.17 |
| 2598625 | 11/1987 | France | 604/174 |
| 8804185 | 6/1988 | World Int. Prop. O. | 604/174 |

OTHER PUBLICATIONS

"New Inventions", *The Lancet*, Dec. 23, 1961, p. 1388.

*Primary Examiner*—Edgar S. Burr
*Assistant Examiner*—Eric P. Raciti
*Attorney, Agent, or Firm*—Gunn Lee & Miller

[57] ABSTRACT

An oral airway (10) for providing fluid communication through a patient's mouth and into the patient's trachea. The oral airway (10) includes a tubular body (12) having a near end (14) and a removed end (16), the near end (14) having a plate (22) with an elliptical perimeter defining resilient lips (36) with semicircular walls (28) forming a C-shaped opening to releasably retain an endotracheal tube (38).

6 Claims, 3 Drawing Sheets

ORAL AIRWAY FOR DEMOUNTABLY ATTACHING AN ENDOTRACHEAL TUBE

FIELD OF THE INVENTION

Oral airways, specifically an oral airway comprising a tubular body with a plate at one end thereof, the plate having perimeter walls defining resilient lips for releasably retaining an endotracheal tube.

BACKGROUND

An oral airway is used in medicine to provide an artificial passageway through the human mouth and into the beginning of the trachea. That is, oral airways are used by physicians and nurses to maintain gaseous communication between the lungs of a breathing patient and his environment. The use of oral airways prevents, for example, the tongue from blocking the air passage and preventing the patient from breathing.

Typical of the oral airways presently in use is that manufactured by Hudson Respiratory Care, Inc., 27711 Dias Road, Tomacula, Calif., 92589 as Model 1169. This particular oral airway is comprised of a substantially curved tubular body represented with a plate mounted at one end thereof. The general dimensions of this particular model oral airway may be appreciated from viewing FIG. 4.

Frequently, with Intensive Care Unit (ICU) patients or ventilator patients, endotracheal tubes are used in conjunction with oral airways. Endotracheal tubes are used to provide communication between the patient's external environment and the patient's lungs.

The use of oral airways such as the Hudson Respiratory Oral Airway with the endotracheal tube requires that the tube be taped to the oral airway twice at the same point just below the plate of the oral airway, in the manner illustrated in FIG. 4. That is, the two devices must be stabilized together with a first taping just below the flange plate as in FIG. 4. The second taping begins at the same location but extends around the patient's neck and back to the now unitized edotracheal tube/oral airway combination. The second taping maintains the position of the combination with respect to the carina, such that the distal end of the endotracheal tube stops 1½ inches above the carina. It is the improved oral airway of the present invention that obviates the need for the first taping, stabilizing the two together yet providing the additional feature of walls to prevent side to side motion of the endotracheal tube with respect to the oral airway.

However, physicians and ICU nurses have long complained when having to use the oral airways in conjunction with the endotracheal tubes. The inability to effectively stabilize the two devices together with tape has resulted in excessive taping, dislodgement, sliding, or misplacement of the tubes. This is especially dangerous because it is important that the tube be properly positioned and maintained at about 1½ inches above the carina. When the endotracheal tube is taped to the oral airway for stabilization, the tape also provides a warm and moist site conducive to the growth of bacteria and other pathogens. Moreover, the use of a tape to stabilize the endotracheal tube oral airway juncture in a moist environment such as the patient's mouth, provides a means for slippage when saliva from the patient lubricates the adhesive surface of the tape.

What is needed is a means for providing an oral airway that is quickly detachable (without the disadvantages of tape) to, and will securely maintain its position with, the endotracheal tube. This is especially important where time is critical, as with a patient in a crisis condition, and with ICU patients or ventilator patients.

Thus, what is needed is an oral airway that may be easily, quickly, securely, and without the aid of tools, capable of releasably attaching to an endotracheal tube.

OBJECTS OF THE PRESENT INVENTION

It is the object of the present invention to provide for an oral airway capable of demountably attaching, without the use of tools, to an endotracheal tube.

It is another object of the present invention to provide for an oral airway made up of a curved tubular body with the plate at a first end thereof, the plate having a perimeter thereon with walls defining lips, the lips being resilient and dimensioned to releasably retain an endotracheal tube.

SUMMARY OF THE INVENTION

The objects of the present invention are provided for in an oral airway for providing fluid communication through a patient's mouth and into the patient's trachea. The oral airway is comprised of a tubular body having a near end and a removed end, the near end being comprised of a plate with an elliptical perimeter defining resilient lips with semicircular walls forming a C-shaped opening to releasably retain an endotracheal tube.

DETAILED DESCRIPTION OF THE PREFERRED EMBODIMENT

Figure 1:
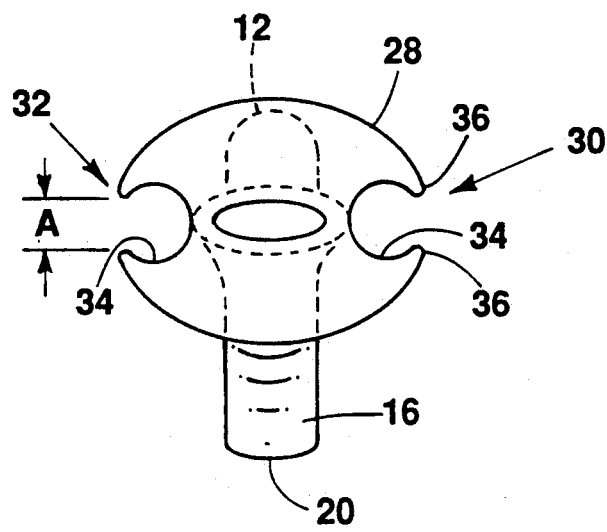
FIG. 1 illustrates a top elevational view of the oral airway of the present invention.
Figure 2:
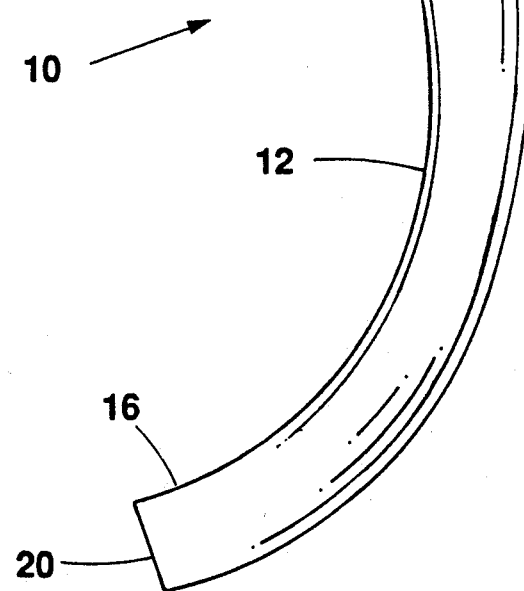
FIG. 2 illustrates a side elevational view of the oral airway of the present invention.

FIGS. 1 and 2 illustrate a top and side elevational view of the general shape of oral airway (10) of Applicant's present invention. More specifically, FIGS. 1 and 2 illustrate oral airway (10) having an arcuate body (12) with a near end (14) and a removed end (16). Near end (14) defines a first opening (18); and removed end (16) defines a second opening (20). Arcuate body (12) is hollow, providing fluid communication between first opening (18) and second opening (20). Integral with first opening (18) at near end (14) is flange plate (22). As can be seen in FIGS. 1 and 2, flange plate (22) is further comprised of top surface (24) and bottom surface (26), the top surface (24) and bottom surface (26) being joined at outer perimeter walls (28).

As is appreciated from FIG. 1, outer perimeter walls (28) define first attachment means (30) and second attachment means (32), the attachment means being similarly dimensioned and having perimeter clamp walls (34) joining outer perimeter walls (28) to define lips (36). Thus, first (30) and second (32) attachment means provide for walls defining a C-shaped opening dimensioned to enclosingly grasp an endotracheal tube inserted therethrough.

As can be seen in FIGS. 1 and 2, the shape of oral airway body (12) is arcuate, providing a shallow bend that generally describes the curvature of the upper throat. Flange plate (22) is flat and joined with near end (14) perpendicular to the longitudinal axis of first opening (18). Flange plate (22) serves to prevent oral airway (10) from entering the patient's throat, and is normally mounted flush with the patient's lips to provide a passageway for air or fluids moving through first opening (18) and second opening (20).

Figure 3:
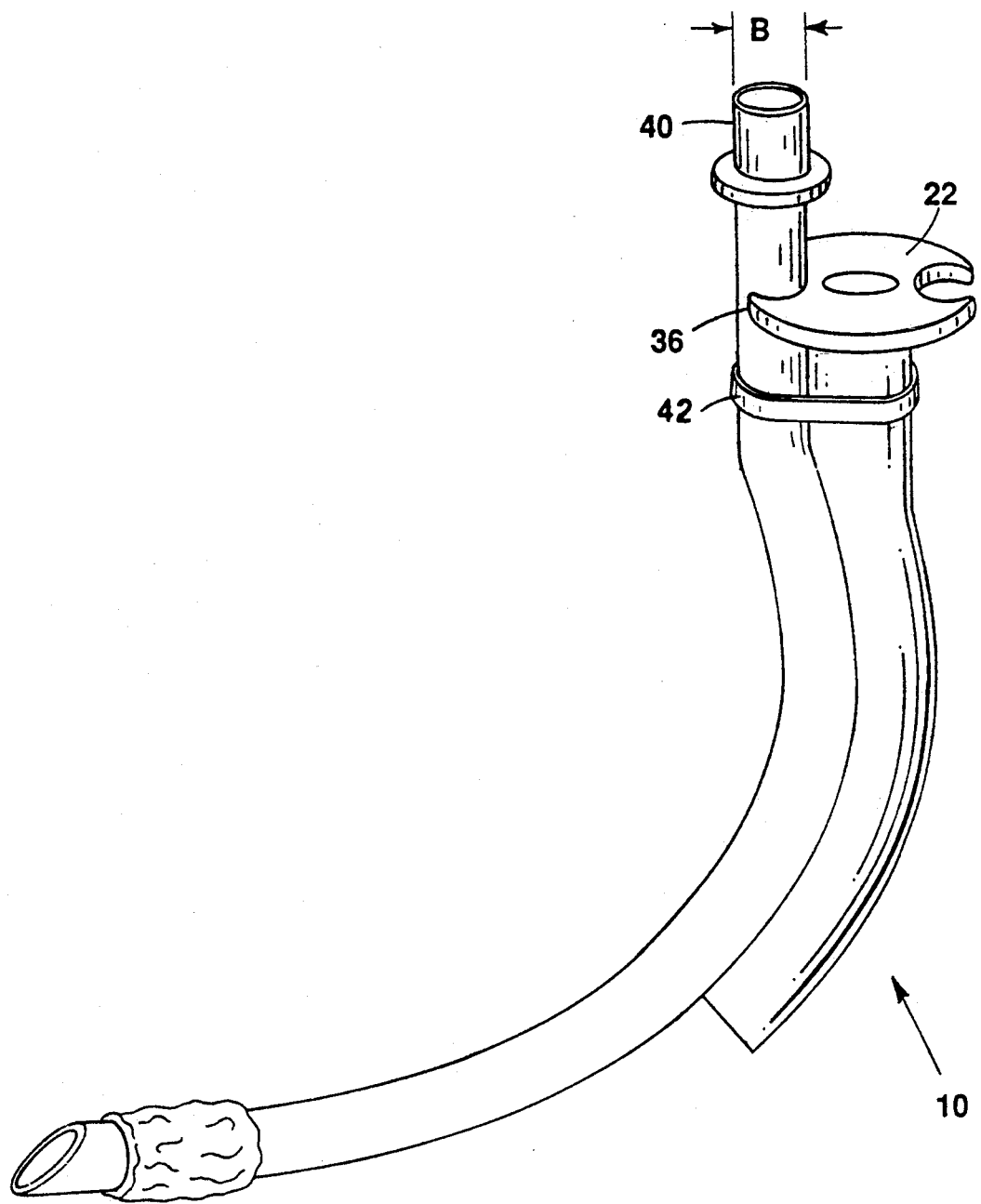
FIG. 3 illustrates in perspective view of the present invention and how it is fastened to the endotracheal tube.

As can be appreciated from FIG. 1, the physical dimensions of plate (22) are varied to generally meet the needs of the patient. The dimensions are sized to fit neonatal, infant, child and adult patients. As can be further appreciated in FIG. 1, the cross-section of arcuate body (12), first opening (18) and second opening (20), as well as flange plate (22) is oval. At the two removed apexes of oval flange plate (22) can be found lips (36). The distance between each oppositely disposed pair (dimension A in FIG. 1) should be less than the outside diameter of endotracheal tube (38) (see FIG. 3) such that it "snaps" on as illustrated in FIG. 3. More specifically, the dimensions B as illustrated in FIG. 3 signifies the outer diameter of endotracheal tube (38) which are typically in the range 2.0 to 9.0 millimeters. The radius of curvature of the C-shaped openings defined by perimeter clamp walls (34) and outer perimeter walls (28) to form first and second attachment means (30) and (32), respectively, should be about the same as or just slightly less than one-half the diameter described by dimension B in FIG. 3, that being the outside diameter of endotracheal tube (38). Attachment means (30) and (32) may have the same radius of curvature or one may be larger than the other. In any case, attachment means (30) and (32) cannot in anyway obstruct or pinch endotracheal tube (38). Moreover, it can be appreciated from viewing FIG. 3 that lips (36) should have a linear distance between them that is less than the outside diameter B and also that the lips, and indeed plate (22), should preferably be made of a resilient material (such as plastic) to allow a "snap fit" with endotracheal tube (38) sliding into first attachment means (30) or (32), depending upon which side the nurse intends to use and provide sufficient tension between perimeter clamp walls (34) and outer surface (40) of endotracheal tube (38) so as to help impede relative motion between endotracheal tube (38) and oral airway (10).

Figure 4:
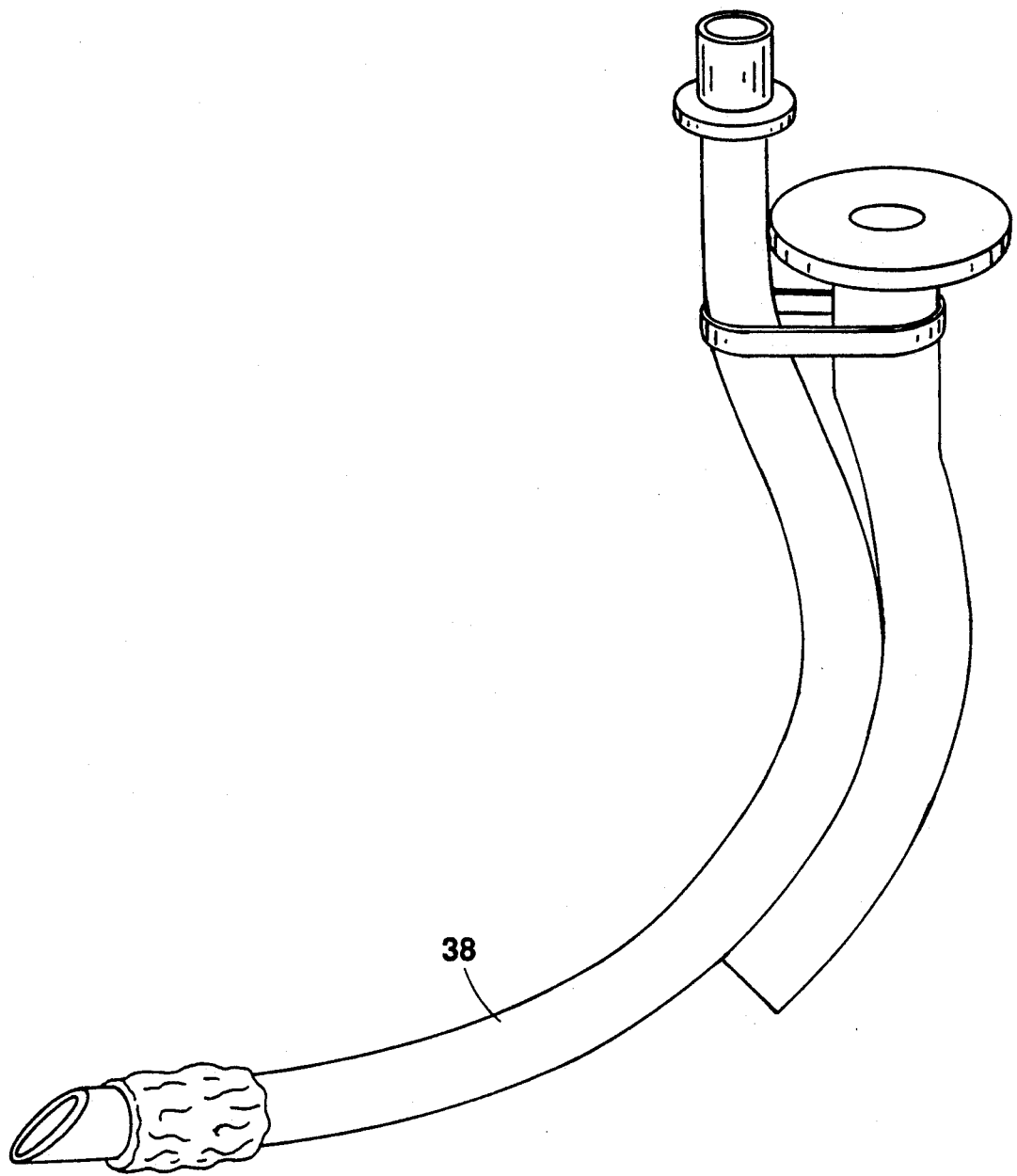
FIG. 4 illustrates the prior art method of attaching an oral airway to the endotracheal tube using tape or other adhesives at two locations between the tube and the airway.

FIG. 3 illustrates the use of oral airway (10) of the present invention. More particularly FIG. 3 illustrates oral airway (10) of the present invention attached to endotracheal tube (38) at lips (36). At a second location along the endotracheal tube/oral airway combination, and below flange plate (22) the two are joined, by tape or other suitable adhesive as indicated at (42). Thus, by use of attachment means (30) or (32) at the near end of oral airway (10) in conjunction with adhesive at second location (42) below flange plate (22) a device the present invention that obviates the need to tape twice, once to connect the endotracheal tube with the oral airway and once to maintain the tubes in the mouth by taping around both tubes (endotracheal and oral airway) and then around the patient's neck. Both tapings are at the same location as illustrated in FIG. 4 (prior art) and prevents the slippage associated with the prior art by providing lips (36) and perimeter clamp walls (34) to prevent any side-to-side movement of endotracheal tube (38) around the perimeter of the oral airway.

Thus, the device of the present invention describes an oral airway for providing fluid communication through a patient's mouth and into the patient's trachea. The oral airway is comprised of a tubular body having a near end and a removed end, the near end being comprised of a plate with an elliptical perimeter defining resilient lips with semicircular walls forming a C-shaped opening to releasably retain an endotracheal tube.

Terms such as "left", "right", "up", "down", "bottom", "top", "front", "back", "in", "out" and the like are applicable to the embodiment shown and described in conjunction with the drawings. These terms are merely for the purposes of description and do not necessarily apply to the position or manner in which the invention may be constructed or used.

Although the invention has been described in connection with the preferred embodiment, it is not intended to limit the invention to a particular form set forth, but on the contrary, it is intended to cover such alternatives, modifications, and equivalents as may be included within the spirit and the scope of the invention as defined by the appended claims.

I claim:

1. An oral airway for providing fluid communication for the passage of gas, for oral suctioning and the like from a patient's mouth through the throat into the trachea and joinable to an endotracheal tube, the oral airway consisting of:

an elongated tubular body having a first open end defining a first orifice and a second open end defining a second orifice;

an annular plate, integral with the first open end of said tubular body, said plate having a top surface and a bottom surface, the top and bottom surfaces joined by a perimeter, the perimeter having walls defining means for demountably attaching an endotracheal tube thereto, wherein the attaching means of said plate comprises a first pair of resilient lips and a second pair of resilient lips formed into a "C" shape, each lip of each of the pairs being oppositely disposed from the other lip of the pair and having a fixed linear distance between them that is less than the outside diameter of the endotracheal tube.

2. The oral airway of claim 1 wherein said plate is comprised of resilient plastic.

3. An oral airway for providing fluid communication from a patient's mouth through the throat into the trachea and joinable to an endotracheal tube, the oral airway consisting of:

an elongated tubular body having a first open end and a second open end;

a ring-shaped plate integral with the first open end of said tubular body and having walls defining a first C-shaped opening and a second C-shaped opening, the first and the second C-shaped openings being oppositely disposed one another on said plate, the plate being made of resilient plastic with the ends of said C-shaped opening defining lips, the distance between the lips being less than the outside diameter of the endotracheal tube.

4. The device of claim 3 wherein the radius of curvature of said C-shaped openings is uniform and is in the range of 0.8 to 4.6 millimeters.

5. The device of claim 3 wherein said body and said plate are comprised of resilient plastic.

6. An oral airway capable of allowing fluid communication from a patient's lips through the mouth to his trachea, the oral airway being detachably joinable with an endotracheal tube, the oral airway consisting of:

an arcuate, tubular body made of non-opaque plastic with walls defining a uniform, oval cross-section and having a first open end and a second open end;

a flange, integral with the first open end of said arcuate, tubular body, said flange being tabular and generally oval in outline, the flange being made resilient plastic and having a thickness in the range of 1.0 millimeters to 3.0 millimeters;

a first endotracheal tube attachment means, said first endotracheal tube attachment means being integral with said flange and being located at one end of the longitudinal axis of said flange, said first endotracheal tube attachment means comprised of walls integral with said flange, the walls defining a C-shaped opening in said flange, the C-shaped opening having a uniform radius of curvature in the range of 0.8 to 4.6 millimeters;

a second endotracheal tube attachment means, said second endotracheal tube attachment means being integral with said flange and being located at one end of the longitudinal axis of said flange, said second endotracheal tube attachment means comprised of walls integral with said flange, the walls defining a C-shaped opening in said flange, the C-shaped opening having a uniform radius of curvature in the range of 0.8 to 4.6 millimeters;

wherein an endotracheal tube may be snap-fit into either of said first or said second endotracheal tube attachment means and stabilized, as with adhesive tape, around the patient's neck position along said body of the oral airway, for insertion into the mount of the patient.

* * * * *